United States Patent [19]

Aoki et al.

[11] 4,192,582
[45] Mar. 11, 1980

[54] OPHTHALMOMETER

[75] Inventors: Mitsugu Aoki; Yoshikazu Konishi; Taketoshi Ishihara, all of Tokyo, Japan

[73] Assignee: Tokyo Kogaku Kikai Kabushiki Kaisha, Tokyo, Japan

[21] Appl. No.: 897,439

[22] Filed: Apr. 18, 1978

[30] Foreign Application Priority Data

Apr. 20, 1977 [JP] Japan .................. 52-45554

[51] Int. Cl.² ............................... A61B 3/02
[52] U.S. Cl. ........................ 351/30; 351/29
[58] Field of Search ............. 351/19, 20, 21, 22, 351/11, 13, 28, 29, 30, 32, 36, 37

[56] References Cited

U.S. PATENT DOCUMENTS 3,969,020  7/1976  Lynn et al. ............... 351/29 X

Primary Examiner—John K. Corbin
Assistant Examiner—Rodney B. Bovernick
Attorney, Agent, or Firm—Stevens, Davis, Miller & Mosher

[57] ABSTRACT

Ophthalmometer comprising a chart projecting optical system for projecting a Landolt type inspection chart and a lens means for locating a corrective lens in the projecting light path. A manually operated switch is provided for actuation by a patient. A mark is presented and moved around the projected chart image for the purpose of having the patient actuate the switch when the mark is at a position corresponding to the slit of the chart. When the switch is actuated at a correct time, the chart advanced by one step but when the switch is actuated at an incorrect timing the lens of next larger dioptral valve is placed in the projecting light path.

4 Claims, 6 Drawing Figures

OPHTHALMOMETER

The present invention relates to ophthalmometers and more particularly to ophthalmometers in which ophthalmoscopic inspections can be proceeded automatically simply through actuation of switches by patients.

In an advanced mode of conventional ophthamoscopic inspections, inspection charts are sequentially projected on a screen and a patient who observes the projected chart makes a reply to the inspector with respect to the visibility of the chart. There is another type of ophthalmometer in which a corrective lens is inserted into the patient's observation optical path so that the patient can observe the projected chart through the corrective lens. In either type of the ophthalmometer, the inspector is required to operate the apparatus in order that the inspection is progressed. Therefore, a substantial time is spent before the inspection is completed.

It is an object of the present invention to provide an ophthalmometer which is convenient for use and by which the ophthalmoscopic inspection can be completed in a decreased time.

Another object of the present invention is to provide an ophthalmometer in which inspection can be proceeded automatically simply through actuation of switches.

According to the present invention, the above and other objects can be accomplished by an ophthalmometer comprising chart projecting optical means having a projecting optical path, ophthalmoscopic inspection chart means having a plurality of inspection charts each including a Landolt ring with a slit, chart advancing means for driving said chart means so that said charts are located in the projecting optical path in sequence one after another whereby an image of the chart in the projecting optical path is produced on a projecting plane, corrective lens means having a plurality of corrective lenses of different dioptral values, lens driving means for driving said corrective lens means so that the corrective lenses are brought into an operative position in sequence one after another, means for providing a mark around the chart image on the projecting plane, means for moving the mark circumferentially around the chart image, manual switch means adapted to be actuated by a patient, discriminating circuit means for discriminating whether the switch means has been actuated when the mark is in a position corresponding to the slit of the projected chart, means connected with the discriminating circuit means for energizing the chart advancing means so that an advanced chart is projected when the switch means is actuated while the mark is in a position corresponding to the slit of the projected mark and for energizing the lens driving means so that a lens having a larger dioptral value is placed in the operative position when the switch means is actuated while the mark is in a position other than the position corresponding to the slit of the projected chart.

Thus, according to the ophthalmometer of the present invention, the inspection can be progressed simply by having the patient actuate the manual switch when the mark is in the position corresponding to the slit of the projected chart. When the switch is actuated at a correct timing, the chart advancing means is energized so that a chart having a smaller Landolt ring is projected for further inspection. When the switch is incorrectly actuated, however, the lens actuating means is energized so that a further inspection is performed using a lens having a larger dioptral value with the same chart.

The present invention can be applied to an ophthalmometer of a type in which the projected chart image is observed by the patient through a corrective lens as well as to a type in which the chart is projected to the patient's eye through a corrective lens.

The above and other objects and features of the present invention will become apparent from the following descriptions of a preferred embodiment taking reference to the accompanying drawings, in which.

Figure 1:
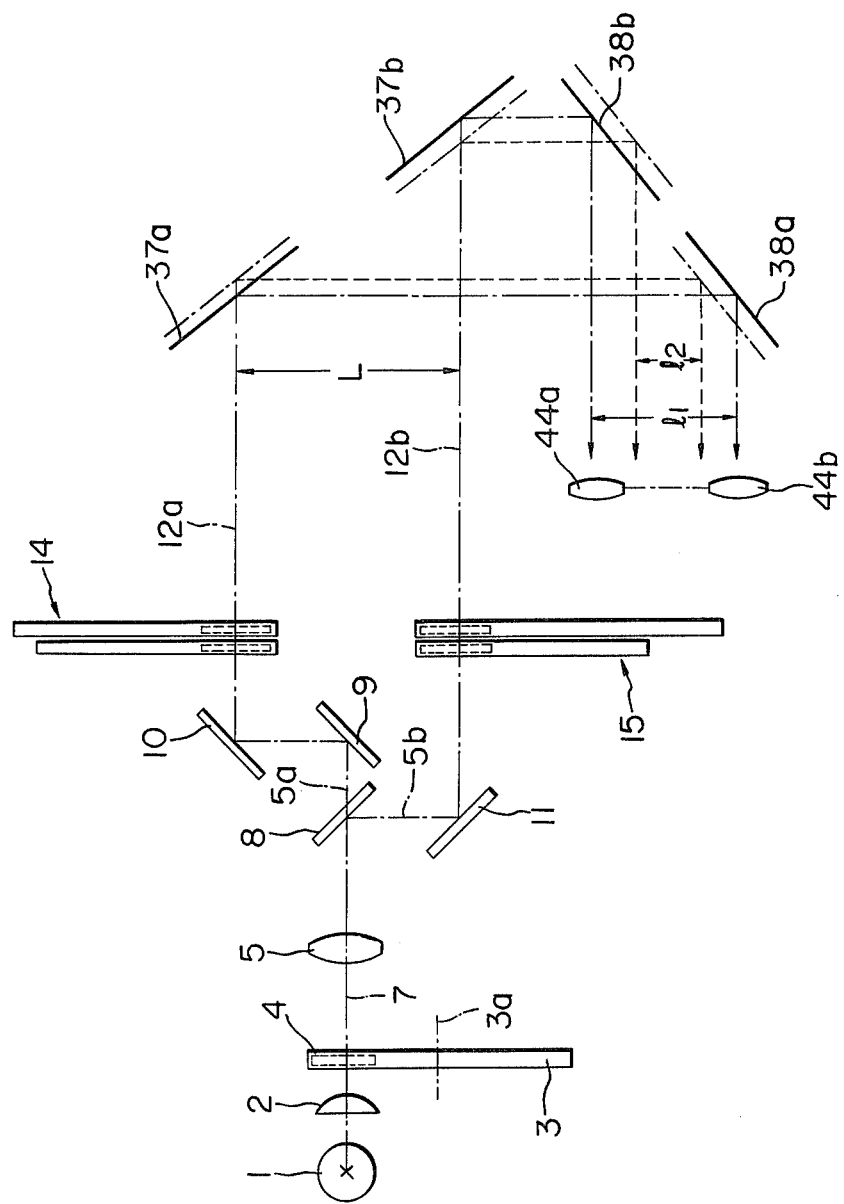
FIG. 1 is a diagrammatical illustration of the chart projecting optical system adopted in the ophthalmometer in accordance with one embodiment of the present invention.
Figure 2:
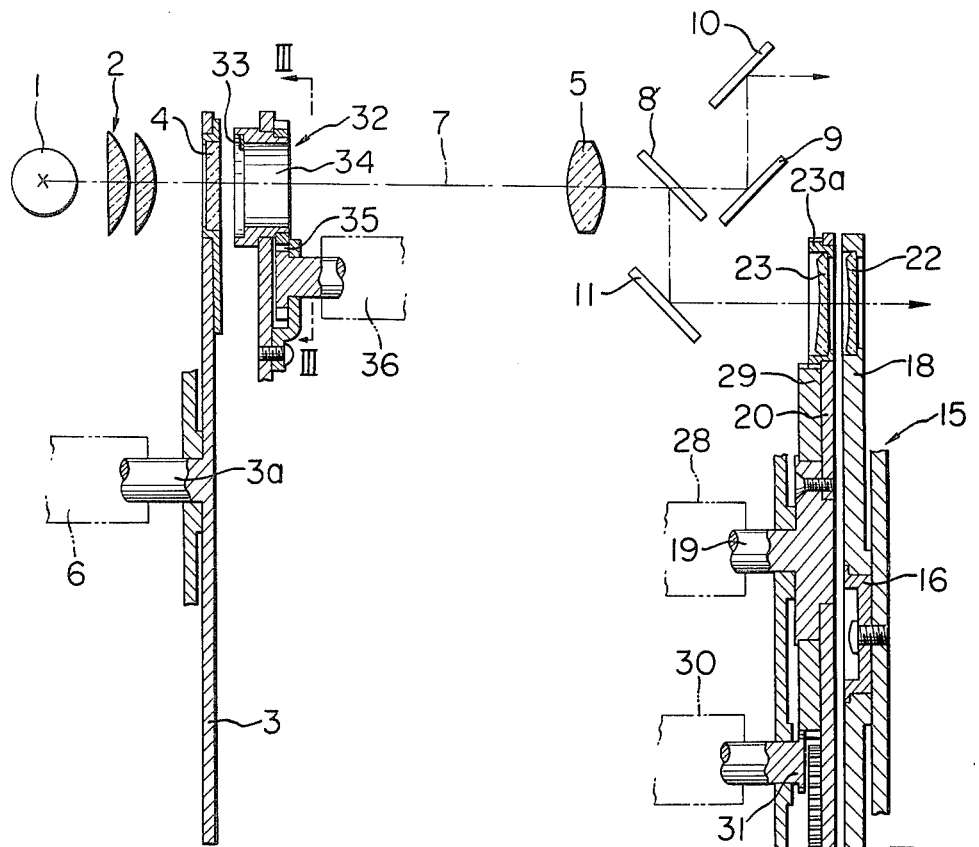
FIG. 2 is a sectional view showing detailed mechanisms adopted in the arrangement shown in FIG. 1.
Figure 3:
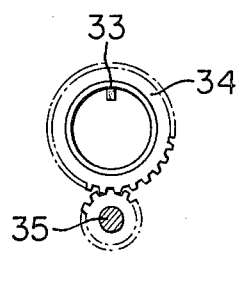
FIG. 3 is a view as seen along the line III—III in FIG. 2.

Referring now to the drawings, particularly to FIG. 1, there is shown a chart projecting system including a light source 1 and a condenser lens 2 for directing the light from the light source 1 along an optical path 7. A plurality of ophthalmoscopic inspection charts 4 are carried on a chart disc 3 which is rotatable about an axis of a shaft 3a and so located that one of the charts 4 is inserted in the optical path 7. As shown in FIG. 2, the shaft 3a is connected with a motor 6 to be driven thereby.

Behind the chart disc 3, there is provided a projecting lens 5 and a half-transparent mirror 8 which are arranged in this order along the optical path 7. A portion of the light along the path 7 is therefore allowed to pass through the mirror 8 along a light path 5a while the remaining portion of the light is reflected by the mirror to pass along a reflected light path 5b.

The light which has passed along the path 5a is then reflected, by a pair of mirrors 9 and 10 provided for the purpose, to pass through an optical path 12a which is parallel with the path 5a. The light passing along the path 5b is reflected by a mirror 11 in the direction of an optical path 12b which is parallel with and laterally spaced from the path 12a by a distance L.

In the optical paths 12a and 12b, there are respectively provided corrective lens devices 14 and 15. Since the lens devices 14 and 15 are the same in construction, only the device 15 is shown in detail in FIG. 2. Referring to FIG. 2, the lens device 15 includes a disc 18 rotatably carried on a stationary shaft 16 and a disc 20 secured to a rotatable shaft 19. The disc 18 carries a plurality to spherical lenses 22 which are arranged with circumferential spacings. Similarly, the disc 20 carries a plurality of cylindrical lenses 23.

Figure 4:
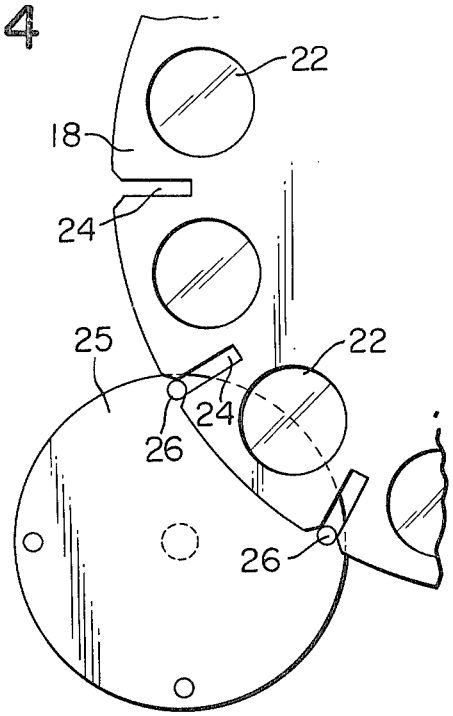
FIG. 4 is a view as seen along the line IV—IV in FIG. 2.

As shown in FIG. 4, the disc 18 has a plurality of radially directed slits 24. A driving disc 25 having a plurality of circumferentially spaced pins 26 is provided adjacent to the disc 18 in such a position that the pins 26 are sequentially brought into engagement with the slits 24 in the disc 18 to drive it. The driving disc 25 is connected with a motor 27 so that the former is rotated by the latter. Thus, the disc 18 is rotated by the motor 27 through the disc 25 and the pins 26 intermittently to locate one of the lenses 22 in the optical path 12b. In the illustrated embodiment, the dioptral value for near or far-sightedness can be measured by the lenses 22.

The disc 20 has a driving shaft 19 which is connected with a motor 28 so that the disc 20 is rotated by the motor. Each of the lenses 23 is mounted in a lens frame 23a which is in turn rotatably mounted on the disc 20. The lens frame 23a has external gear teeth which are adapted to engage with a gear 29 rotatably supported about the driving shaft 19. The gear 29 also engages with a pinion 31 which is driven by a motor 30. Thus, the axis of the cylinder of the lens 23 is rotated by the motor 30.

Referring further to FIG. 2, there is provided an astigmatic index projecting device 32 in the optical path 7 behind the chart disc 3. The device 32 comprises a rotatable member 34 having an index such as a colored mark 33 on a circumferential point thereof. The rotatable member 34 has external teeth which are adapted to be engaged with a pinion 35 driven by a motor 36. The motor 36 may be controlled by a switch which may be actuated by a patient and the astigmatic axis of the patient's eye can be determined by locating the index 33 is at the circumferential position of the projected chart where the projected image can be most clearly observed.

Referring back to FIG. 1, mirrors 37a and 37b are disposed respectively in the optical paths 12a and 12b with inclination angles of 45° with respect to the optical paths and a further pair of mirrors 38a and 38b are provided so as to reflect the lights from the mirrors 37a and 37b in the directions parallel but opposite to the optical paths 12a and 12b. As shown in FIG. 1, the mirrors 37a and 37b are respectively associated with the mirrors 38a and 38b so as to move together and by moving the mirrors from the positions shown by solid lines to the positions shown by dotted lines the lateral distance between the two optical paths can be decreased from $l_1$ and $l_2$. The light bundles which have been reflected by the mirrors 38a and 38b are passed through focusing lenses 44a and 44b to be focused. As is well known in the art, in this type of ophthalmometer, the patient's eyes are positioned at a predetermined distance from the focusing lenses 44a and 44b to observe the projected images of the chart 4 through the corrective lenses in the lens device 14 and 15.

Figure 5:
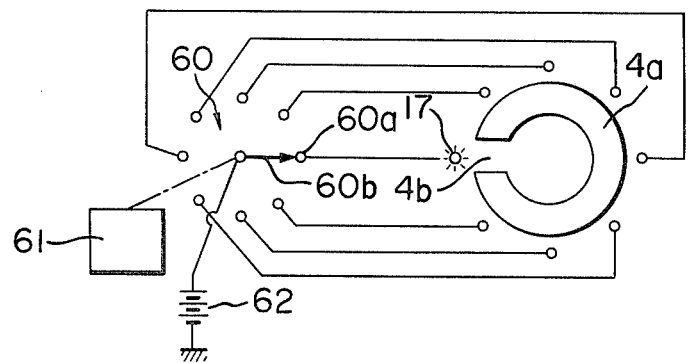
FIG. 5 is view showing a projected chart and a mark around the chart.

Referring to FIG. 5, it will be noted that the chart 4 includes a mark 4a in the form of a ring having a slit 4b, which is well known in the art as the Landolt ring. The charts 4 on the disc 3 respectively have such Landolt rings 4a which differ in diameter among the charts 4. A provision is made in such a manner that marks 17 are sequentially presented around the projected chart one after another at predetermined circumferential distances. In the example shown in FIG. 5, small light sources such as light emitting diodes (LED) are arranged in such a way that the lights or images of lights from the light sources 17 are located around the projected chart images at 45° angular distances. The light sources 17 may be located anywhere in the chart projecting optical path. When the chart image is projected on a screen so that it is observed by a patient, the light sources may be provided on the screen.

The light sources 17 are respectively connected with stationary contacts 60a of a rotary switch 60 which has a rotatable contact 60b adapted to be driven by a motor 61 and connected with an electric power source 62. Thus, it will be noted that, as the rotatable contact 60b is rotated by the motor 61, the light sources 17 are energized sequentially one after another.

Figure 6:
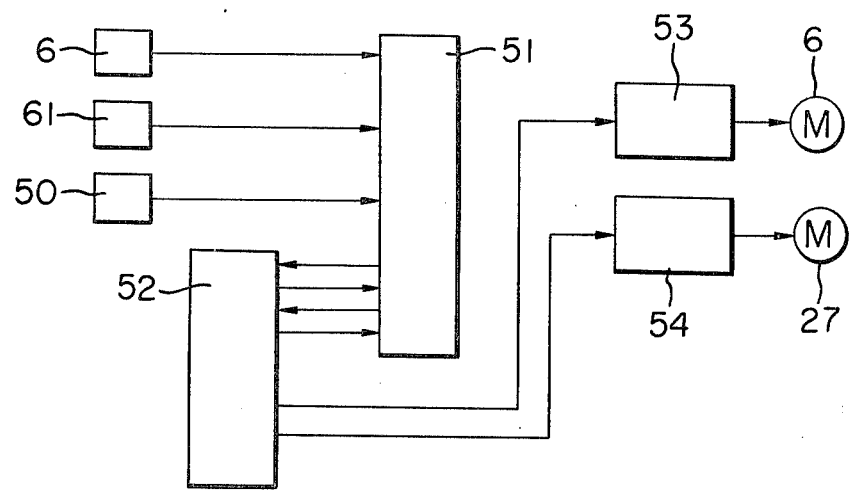
FIG. 6 is a block diagram showing the control circuit in accordance with one embodiment of the present invention.

According to a feature of the present invention, there is provided a manually operated switch 50 which is adapted to be operated by a patient. As shown in FIG. 6, the switch 50 is connected with a discriminating circuit 51 which is also connected with the motors 6 and 61 so as to receive motor position signals therefrom. The discriminating circuit 51 functions to judge in accordance with the signals from the switch 50 and the motors 6 and 61 whether the switch 50 has been actuated when the light source 17 corresponding to the slit 4b on the Landolt ring 4a is energized. The circuit 51 thus produces a correct or error signal which is transferred to a control circuit 52. The control circuit 52 has output lines which are respectively connected with a motor control circuits 53 and 54 for controlling the chart advancing motor 6 and the lens driving motor 27, respectively.

The control circuit 52 functions to produce a chart advance signal when the correct signal is received from the discriminating circuit 51 and send the chart advance signal to the chart motor control circuit 53 which energizes the motor 6 so that the chart disc 3 is rotated by one step to present a next or advanced chart 4 in the projecting optical path. When the error signal is received, the control circuit 52 functions to produce a lens drive signal which is applied to the lens motor control circuit 54 to energize the motor 27 so that the lens disc 18 is rotated to present another lens of next larger dioptral value in the projecting optical path.

It will be noted from the above descriptions that the ophthalmoscopic inspection can be proceeded substantially automatically simply by having the patient push the manual switch. The total inspection time can thus be significantly decreased and a reliable measurement can be accomplished.

The invention has thus been shown and described with reference to a specific embodiment, however, it should be noted that the invention is in no way limited to the details of the illustrated arrangement but changes and modifications may be made without departing from the scope of the appended claims.

We claim:

1. Ophthalmometer comprising chart projecting optical means having a projecting optical path, ophthalmoscopic inspection chart means having a plurality of inspection charts each including a Landolt ring with a slit, chart advancing means for driving said chart means so that said charts are located in the projecting optical path in sequence one after another whereby an image of the chart in the projecting optical path is produced on a projecting plane, corrective lens means having a plurality of corrective lenses of different dioptral values, lens driving means for driving said corrective lens means so that the corrective lenses are brought into an operative position in sequence one after another, means for providing a mark around the chart image on the projecting plane, means for moving the mark circumferentially around the chart image, manual switch means adapted to be actuated by a patient, discriminating circuit means for discriminating whether the switch means has been actuated when the mark is in a position corresponding to the slit of the projected chart, means connected with the discriminating circuit means for energizing the chart advancing means so that an advanced chart is projected when the switch means is actuated while the mark is in a position corresponding to the slit of the projected chart and for energizing the lens driving means so that a lens having a larger dioptral value is placed in the operative position when the switch means is actuated while the mark is in a position other than the position corresponding to the slit of the projected chart.

2. Ophthalmometer in accordance with claim 1 in which said corrective lens means is located along the projecting optical path so that the lens in the operative position is in the projecting optical path whereby the chart is projected through the lens.

3. Ophthalmometer in accordance with claim 1 in which the mark providing means includes a plurality of light sources arranged to provide lights around the projected chart.

4. Ophthalmometer in accordance with claim 1 in which said mark providing means is disposed in the projecting optical path.

* * * * *